(12) United States Patent  
Ellman et al.

(10) Patent No.: US 6,352,533 B1  
(45) Date of Patent: Mar. 5, 2002

(54) ELECTROSURGICAL HANDPIECE FOR TREATING TISSUE

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/483,994

(22) Filed: Jan. 18, 2000

Related U.S. Application Data

(63) Continuation-in-part of application No. 09/303,834, filed on May 3, 1999, now Pat. No. 6,231,571, which is a continuation-in-part of application No. 09/393,286, filed on Sep. 10, 1999, now Pat. No. 6,210,409, which is a continuation-in-part of application No. 09/425,313, filed on Oct. 25, 1999.

(51) Int. Cl.[7] .............................................. A61B 18/18  
(52) U.S. Cl. ............................ 606/41; 606/45; 606/48; 606/49; 606/50  
(58) Field of Search ............................. 606/34, 37, 39, 606/40, 110, 113, 162, 41, 45, 46, 47, 48, 49, 50

(56) References Cited

U.S. PATENT DOCUMENTS

| | | | | |
|---|---|---|---|---|
| 5,290,286 A | * | 3/1994 | Parins | 606/50 |
| 5,733,283 A | | 3/1998 | Malis et al. | |
| 5,848,986 A | * | 12/1998 | Lundquist et al. | 604/22 |
| 6,206,876 B1 | * | 3/2001 | Levine et al. | 606/45 |

* cited by examiner

*Primary Examiner*—R. Kearney

(57) ABSTRACT

A bipolar electrosurgical handpiece, and electrode for use with the handpiece, that is configured for use in MIS and other electrosurgical procedures. The handpiece is constructed with a flexible end controllable by the surgeon so as to allow the surgeon to manipulate the end as desired during the surgical procedure. The electrode is housed in a tubular member. The electrode ends comprise bare loops projecting from the end of the housing in spaced parallel planes. When energized, a bipolar discharge is generated between the bare loops.

9 Claims, 3 Drawing Sheets

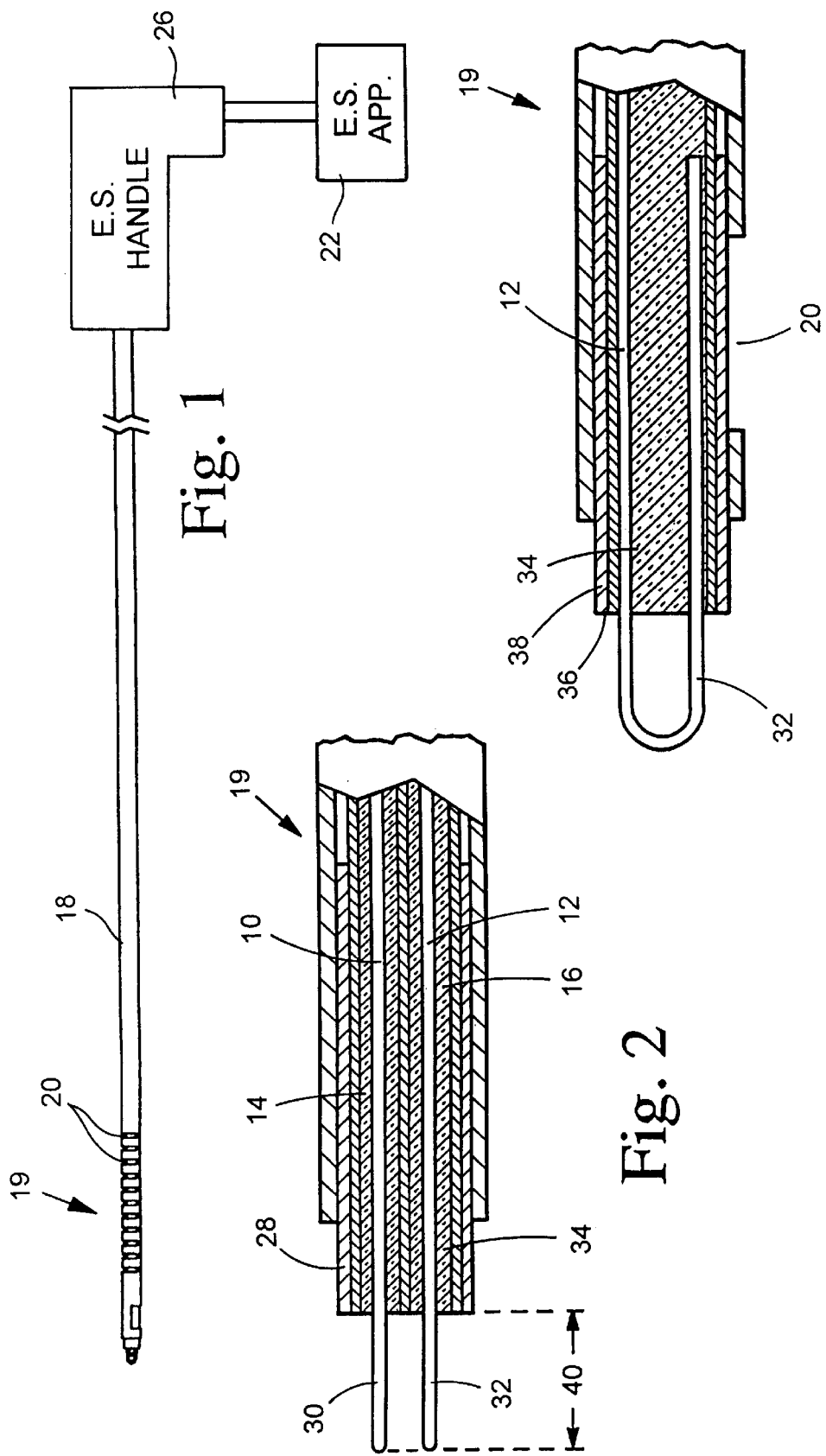

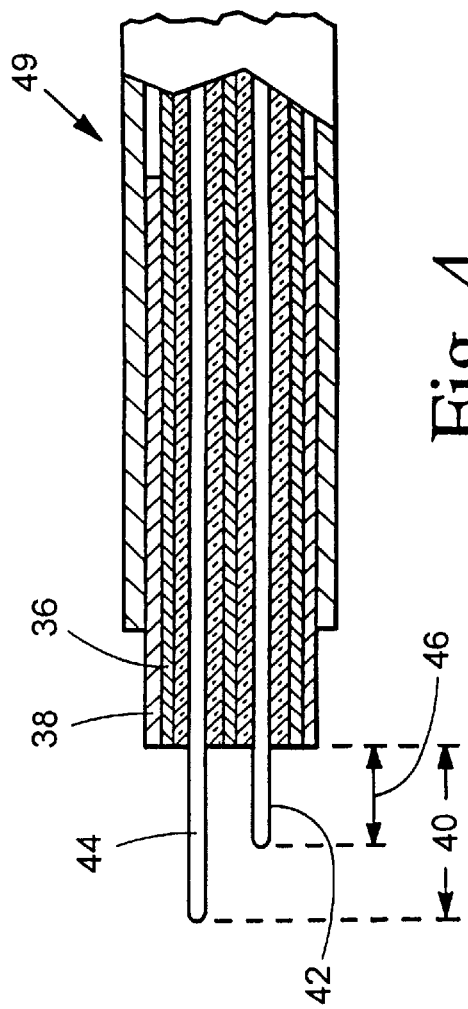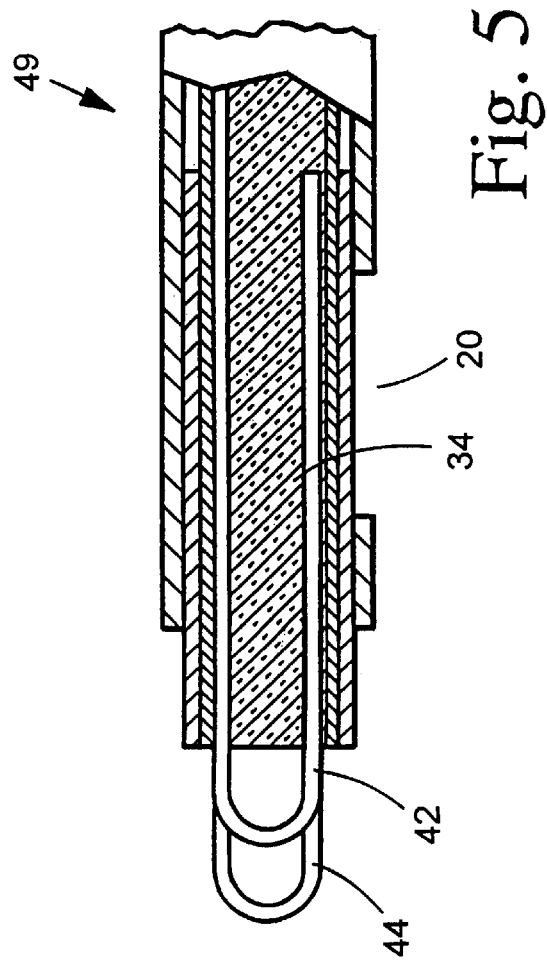

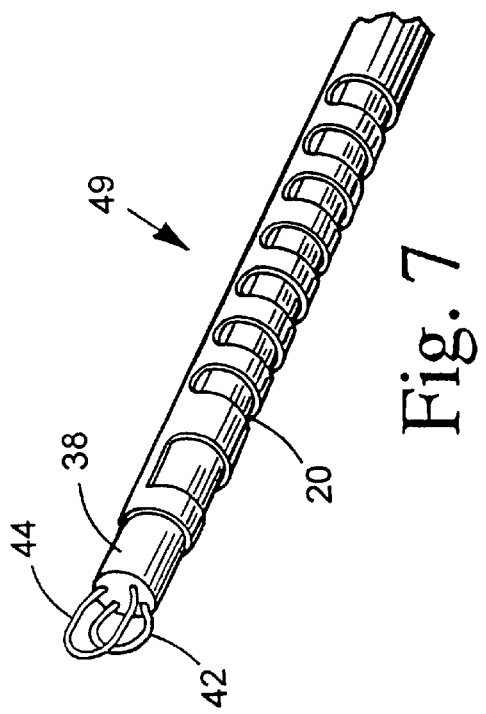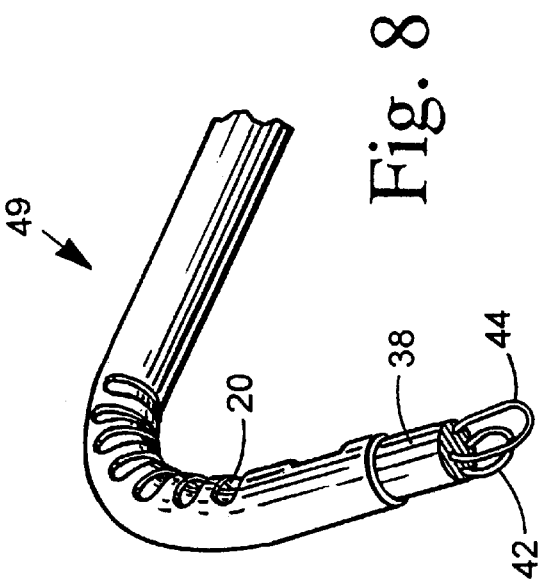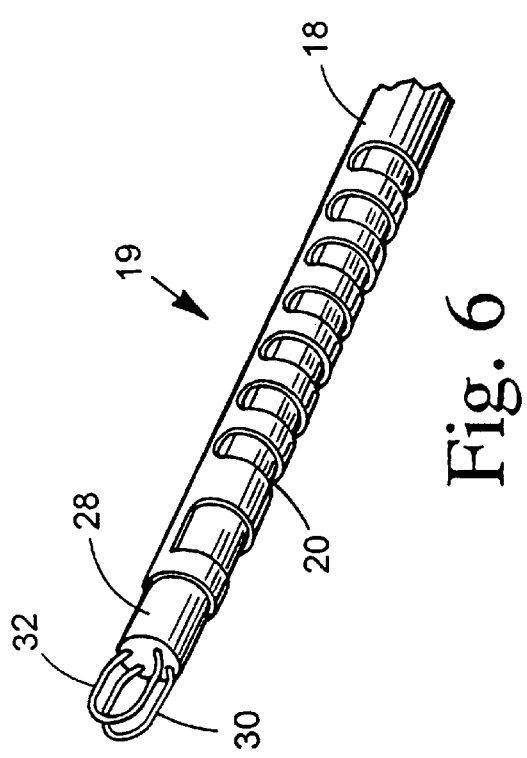

ELECTROSURGICAL HANDPIECE FOR TREATING TISSUE

RELATED APPLICATION

U.S. application, Ser. No. 09/303,839, filed May 3, 1999, U.S. Pat. No. 6,231,571 commonly owned, for "Electrosurgical Handpiece For Treating Tissue", of which the present application is a continuation-in-part.

U,S. application, Ser. No. 09/393,286, filed Sep. 10, 1999, U.S. Pat. No. 6,210,409 commonly owned, for "Electrosurgical Handpiece For Treating Tissue", of which the present application is a continuation-in-part.

U.S. application, Ser. No. 09/425,313, filed Oct. 25, 1999, commonly owned, for "Electrosurgical Handpiece For Treating Tissue", of which the present application is a continuation-in-part.

This invention relates to an electrosurgical handpiece and an activator for an electrosurgical handpiece.

BACKGROUND OF THE INVENTION

Our prior application, Ser. No. 09/303,839, describes a novel electrosurgical handpiece for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. Preferably, the handpiece is provided with a dual compartment insulated elongated tube, each of the compartments serving to house one of the two wires of the bipolar electrodes. The electrode for MIS use is preferably constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In FIGS. 3–7 of the prior application, a suitable bipolar electrode is described. FIGS. 8–10 illustrate a suitable unipolar electrode construction of the flexible end handpiece. FIG. 12 illustrates how such an electrode can be used for the reduction of herniated disks in a laparoscopic procedure. FIG. 20 shows a scissors end that can be constructed as a bipolar electrode for certain purposes.

Our prior application, Ser. No. 09/393,286, describes a modified bipolar electrode construction using the flexible end handpiece, the modified bipolar electrode having spaced prongs.

Our prior application, Ser. No. 09/425,313, describes a modified bipolar electrode configured to provide easier flexing of the handpiece end, or more controlled flexing and positioning of the handpiece end.

In these prior applications, the handpiece end is made flexible by providing a spaced set of slots at the handpiece end, such that, when a pulling wire attached to the handpiece end is pulled by the surgeon, the end bends or flexes in a direction toward the slotted side.

SUMMARY OF THE INVENTION

The present invention is a continuation-in-part of the three prior applications and hereby incorporates by reference the total contents of the three prior applications, Ser. Nos. 09/303,839, 09/393,286 and 09/425,313. The present invention describes a novel handpiece end construction that offers certain benefits not readily obtainable with the constructions of the prior applications. Since the present application otherwise makes use of the same teachings of the prior applications, it was felt unnecessary to repeat in the body of this specification many of the details present in the contents of the prior application. The present description will be confined solely to the differences in the handpiece ends to achieve certain benefits that may be more difficult to achieve with the constructions of the prior applications. For more details, the reader is directed to the prior applications.

The new handpiece end constructions of the present improvement uses the bipolar principle and are configured to provide more controlled distribution of the electrosurgical currents to the tissue to be modulated.

In a preferred embodiment, the electrode ends are formed by axially-projecting, dual spaced wire loops each connected to a terminal of the bipolar source. In a first preferred embodiment, the wire loops project in spaced parallel planes approximately the same distance from the insulated end of the electrode. In a second preferred embodiment, the wire loops project different distances from the electrode end.

It is also possible within the scope of the invention for the wire loops to lie in spaced non-parallel planes.

The constructions of the invention will provide the same important benefits not only for MIS of herniated disks but also for other MIS procedures where controlled electrode position and controlled heat generation is of importance as described in the prior applications, as well as for general electrosurgical procedures where the volumetric reduction of tissue is desirable.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a schematic view of one form of electrosurgical handpiece in accordance with the invention. The working end is shown in its non-flexed position;

FIG. 2 is an enlarged cross-sectional view of the electrode end of FIG. 1;

FIG. 3 is an enlarged cross-sectional view of the electrode end of FIG. 1 taken from a position rotated 90° with respect to the FIG. 2 view;

FIG. 4 is an enlarged cross-sectional view of the electrode end of a modification;

FIG. 5 is an enlarged cross-sectional view of the electrode end of FIG. 4 taken from a position rotated 90° with respect to the FIG. 4 view;

FIG. 6 is an enlarged perspective view of the working end of the handpiece of FIG. 1;

FIG. 7 is an enlarged perspective view of the working end of the handpiece of FIG. 4;

FIG. 8 is an enlarged perspective view of the working end of the handpiece of FIG. 4 but with the end in its flexed position.

DETAILED DESCRIPTION OF THE PREFERRED EMBODIMENTS

The reader is directed to the referenced prior applications for a more detailed description of the prior applications which will assist in understanding the improvements offered by the present application.

In the present application, the gun configuration remains essentially the same. The only changes made are the construction of the active electrode at the flexible end. As in the earlier applications, for the bipolar handpiece, two electrically-insulated wires 10, 12 are passed through insulated compartments 14, 16 of a tubular housing 18 (see FIGS. 1–3 and 6) whose distal end 19 is weakened as by spaced slots 20 and thereby made flexible. A third wire (not shown) is connected to the movable trigger (not shown) of a gun-type housing having a fixed handle 26. The two wires 10, 12 are not only insulated from each other so that bipolar electrosurgical voltages can be applied between them, but they are also insulated from the tubular housing 18 which may be of metal. The latter insulation may be in the form of a flexible plastic tube 28. The two wires 10, 12 which preferably are of round fine wire terminate in a pair of bare, i.e., not insulated laterally-spaced metal loops 30, 32 which serve as the active bipolar electrodes of the handpiece working end and which axially project from the end of the plastic tube 28 in spaced parallel planes. That is to say, each loop is in a plane which is spaced laterally from the plane of the other loop. By "axial" is meant parallel to the long axis of the electrode (horizontal in FIGS. 1 and 2). By "lateral" is meant transverse to the long axis of the electrode (vertical in FIGS. 1 and 2). In FIG. 6 the loops 30, 32 are shown in their normal working position. The two insulated wires 10, 12 terminate at the right hand of the gun 26 in a connector (not shown) having prongs which can be plugged into the standard bipolar cable which connects the gun to electrosurgical apparatus 22. The pulling wire (not shown) is anchored as by welding to the flexible end at, for example, a bottom point (when the bending is to occur downward). When the surgeon while holding the gun handle 26 squeezes the trigger, the wire is pulled flexing the end 19. The surgeon can manipulate the position of the electrodes 30, 32 by the the pulling force exerted on the pulling wire.

The position of the pulling wire and that of the slots can be oriented in various planes to control the plane of flexing.

Once the surgeon has positioned the working end of the handpiece with respect to the tissue to be operated on, he or she then activates the electrosurgical apparatus causing a discharge of bipolar currents between the bare electrode loop ends 30, 32 capable of causing excision of tissue or cauterization of a blood vessel in the usual way positioned between the loop ends. Other usable mechanical or electrical structures following the teachings of the prior applications will be appreciated by those skilled in this art. As with the embodiments of the prior application, the insulating tube 28 will prevent accidental touching of patient tissue by the electrode sides, so that the bipolar discharge is localllized to the spacing between the bare ends 30, 32.

In all embodiments, the tubular housing 18 can be of relatively stiff metal that will not bend except where desired at the area of the slots 20. For example, a suitable metal is stainless steel and a suitable tube wall thickness is about 0.002–0.01 inches. The tube outside diameter is typically about 0.04–0.1 inches. The two wire ends forming each loop can be spaced apart in its plane about 0.02–0.05 inches, preferably about 0.0375 inches. The radius of each loop is about one-half the latter dimension. The two loops can be spaced apart in a direction perpendicular to their respective planes about 0.013–0.025 inches, preferably about 0.0187 inches. The insulation between the two wires 30, 32 can be provided, for example, by internal glue 34, a plastic tube 36, and a heat-shrunk tube 38. Other electrically-insulating materials can be substituted. For the application of shrinking herniated tissue via a cannula, the tubular housing is typically about 15–20 inches long.

In the first embodiment of FIGS. 2 and 3, the two wires 30, 32 extend the same distance from the free end of the insulating tubes 36, 38. This distance, indicated in FIG. 2 by reference numeral 40, measured along the longitudinal axis of the tube 18, is about 0.05–0.09 inches, preferably about 0.075 inches.

In the second embodiment of FIGS. 4, 5, 7 and 8, the two wires 42, 44 are offset axially from one another in the two parallel planes and thus extend different distances from the free end of the insulating tubes 36, 38. One wire 44 extends, for example, about the same distance 40 as the wires in the first embodiment, namely, about 0.05–0.09 inches, preferably about 0.075 inches. The other wire 42 extends from the free end of the insulating tubes 36, 38 about one-half the distance, i.e., a distance 46 of about 0.02–0.045 inches, preferably about 0.0375 inches. FIG. 7 shows the second embodiment in its non-flexed position. FIG. 8 illustrates one possible position of the bipolar electrodes 42, 44 when the flexible tip 49 is bent. It will be noted that, in this embodiment, the plane of flexing, shown vertical in FIG. 8, is approximately a vertical plane through the center of the gun and the center of the slots 20.

The slots 20 can be, as described in the copending applications, tapered-wall, parallel-wall or varying-depth slots, or of a spiral or a spring section. The fine loop wire used can be round with a diameter of of about 0.007–0.035 inches, preferably about 0.015 inches.

The preferred embodiments use a metal for the tubular housing. When a bipolar assembly is involved, then the electrode wires have to be insulated from each other and from the metal tube. The 2-compartment electrically-insulating liner tube 36 serves this function. However, in principle, if the electrical connecting wires have their own good electrically-insulating coating, then the insulating liner can be dispensed with.

During operation of the handpiece according to the invention, the electrosurgical currents are concentrated between the sides of the bare wire ends 30, 32 across which the active voltage is developed. When the wires 42,44 are offset, as in the second embodiment, an oblique discharge occurs mostly between the curved distal ends. The electrode is chosen by the surgeon for obtaining the best results during the excision of tissue or blood vessel coagulation.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising:
   (a) an elongated tubular first member having a first end and a distal flexible second end,
   (b) first and second electrically-conductive wires fixedly positioned in electrically-insulating relationship in the first member with first means connected to the first member at its first end for applying to the first and second wires a bipolar electrosurgical voltage capable of generating electrosurgical currents between the wires, each of the first and second wires having a bare end forming a loop projecting out of the first member at its second end,
   (c) the bare end loops of the first and second wires extending in laterally-spaced parallel planes whose relative position in the spaced parallel planes remains fixed whether or not the second end is flexed,
   (d) wherein electrosurgical currents are generated between the spaced bare end parallel loops when the electrosurgical voltage is applied to the first and second wires.

2. The electrosurgical handpiece as claimed in claim 1, wherein the loops of each of the first and second wires project axially about the same distance from the end of the first member.

3. The electrosurgical handpiece as claimed in claim 2, wherein the distance that the loops project axially is about 0.05–0.09 inches.

4. The electrosurgical handpiece as claimed in claim 2, wherein the radius of each loop is about one-half of 0.02–0.05 inches.

5. The electrosurgical handpiece as claimed in claim 2, wherein the two loops are spaced apart in a direction perpendicular to the planes of their loops about 0.013–0.025 inches.

6. The electrosurgical handpiece as claimed in claim 1, wherein the loops of each of the first and second wires project axially different distances from the end of the first member.

7. The electrosurgical handpiece as claimed in claim 4, wherein the loops of each of the first and second wires are made up of fine round wire.

8. An electrosurgical electrode comprising:
   (a) an elongated tubular first member having a first end and a distal second end,
   (b) first and second fixed electrically-conductive wires positioned in fixed electrically-insulating relationship in the first member, each of the first and second wires having a bare end forming a loop projecting out of the first member at its second end,
   (c) the bare end loops of the first and second wires extending in laterally-spaced parallel planes whose relative position in spaced parallel planes remains fixed whether or not the second end is flexed,
   (d) wherein electrosurgical currents can be generated between the spaced bare end parallel loops when an electrosurgical voltage is applied to the first and second wires.

9. The electrosurgical electrode as claimed in claim 3, wherein the loops of each of the first and second wires project about the same distance from the end of the first member.

* * * * *